United States Patent
Stål et al.

(10) Patent No.: US 11,602,645 B2
(45) Date of Patent: Mar. 14, 2023

(54) SYSTEM AND METHOD FOR RADIOTHERAPY TREATMENT PLANNING

(71) Applicant: RaySearch Laboratories AB, Stockholm (SE)

(72) Inventors: Oscar Stål, Stockholm (SE); Erik Engwall, Stockholm (SE); Martin Janson, Stockholm (SE); Lars Glimelius, Stockholm (SE); Erik Traneus, Stockholm (SE); Kjell Eriksson, Stockholm (SE)

(73) Assignee: RaySearch Laboratories AB, Stockholm (SE)

( * ) Notice: Subject to any disclaimer, the term of this patent is extended or adjusted under 35 U.S.C. 154(b) by 201 days.

(21) Appl. No.: 16/668,234

(22) Filed: Oct. 30, 2019

(65) Prior Publication Data

US 2020/0129782 A1    Apr. 30, 2020

(30) Foreign Application Priority Data

Oct. 31, 2018    (EP) .................................... 18203596

(51) Int. Cl.
*A61N 5/10* (2006.01)

(52) U.S. Cl.
CPC ......... *A61N 5/1031* (2013.01); *A61N 5/1067* (2013.01); *A61N 2005/1087* (2013.01)

(58) Field of Classification Search
CPC .... A61N 5/103; A61N 5/1031; A61N 5/1067; A61N 2005/1087
See application file for complete search history.

(56) References Cited

U.S. PATENT DOCUMENTS

| | | | | |
|---|---|---|---|---|
| 2011/0103551 | A1* | 5/2011 | Bal | A61N 5/103 378/65 |
| 2011/0297850 | A1* | 12/2011 | Claereboudt | A61N 5/1044 250/492.1 |
| 2013/0072742 | A1* | 3/2013 | Nord | A61N 5/1031 600/1 |
| 2013/0109904 | A1* | 5/2013 | Siljamaki | A61N 5/1067 600/1 |

(Continued)

FOREIGN PATENT DOCUMENTS

WO    WO-2017156419 A1 *    9/2017    ........... A61N 5/1047

OTHER PUBLICATIONS

Cao, Wenhua et al., "Incorporating deliverable monitor unit constraints into spot intensity optimization in intensity modulated proton therapy treatment planning," Phys Med Biol. Aug. 7, 2013; 58(15): 5113-5125.

(Continued)

*Primary Examiner* — Carrie R Dorna
(74) *Attorney, Agent, or Firm* — Faegre Drinker Biddle & Reath LLP

(57) ABSTRACT

A method of optimizing a radiation treatment plan of ion treatment, in which the optimization procedure is interrupted, some but not all low-weight spots are discarded and the optimization procedure is resumed with a reduced set of spots. The weight of one or more remaining spots may be increased before resuming the optimization procedure, for example by adding the spot weight of one or more of the discarded spots to one or more of the remaining spots.

16 Claims, 2 Drawing Sheets

(56) References Cited

U.S. PATENT DOCUMENTS

| | | | | |
|---|---|---|---|---|
| 2013/0304503 A1* | 11/2013 | Kuefer | .................. | A61N 5/103 705/2 |
| 2014/0005464 A1* | 1/2014 | Bharat | ................ | A61N 5/1031 600/1 |
| 2014/0275696 A1* | 9/2014 | Dempsey | ............ | A61N 5/1077 600/1 |
| 2016/0199667 A1* | 7/2016 | Flynn | .................... | A61N 5/103 600/1 |

OTHER PUBLICATIONS

Howard, Michelle et al., "Effects of minimum monitor unit threshold on spot scanning proton plan quality," Med. Phys. 41(9), Sep. 2014, pp. 091703-1-091703-8.

* cited by examiner

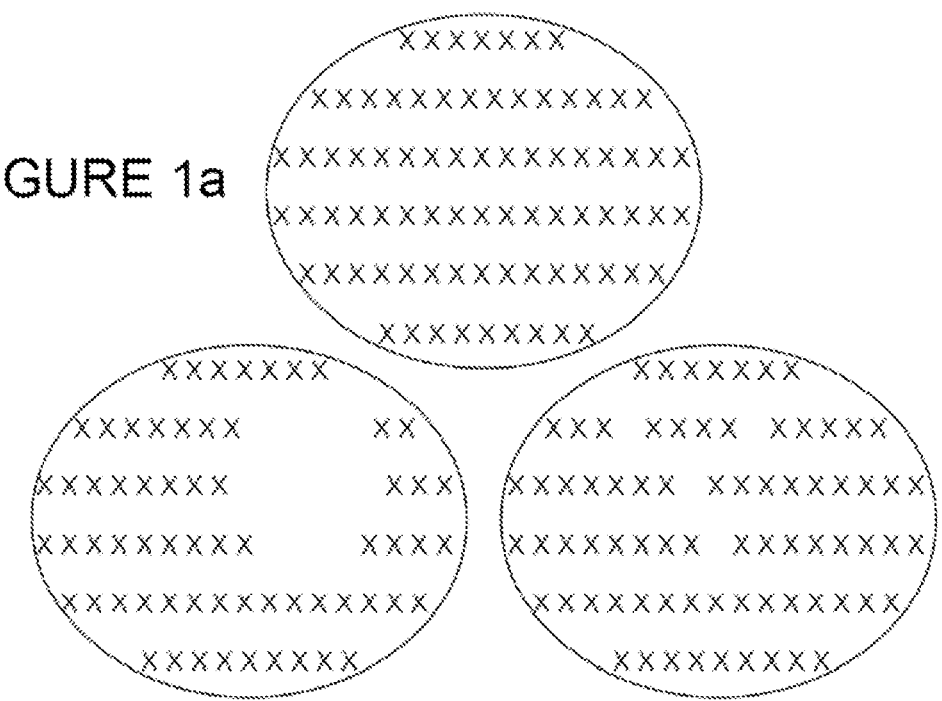
FIGURE 1a
FIGURE 1b
Prior Art
FIGURE 1c
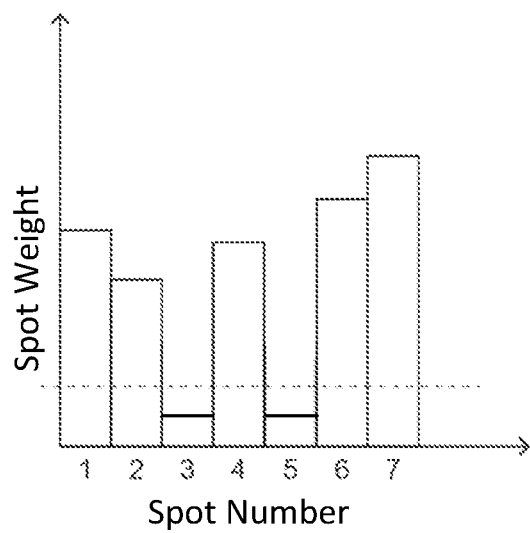
FIGURE 2a
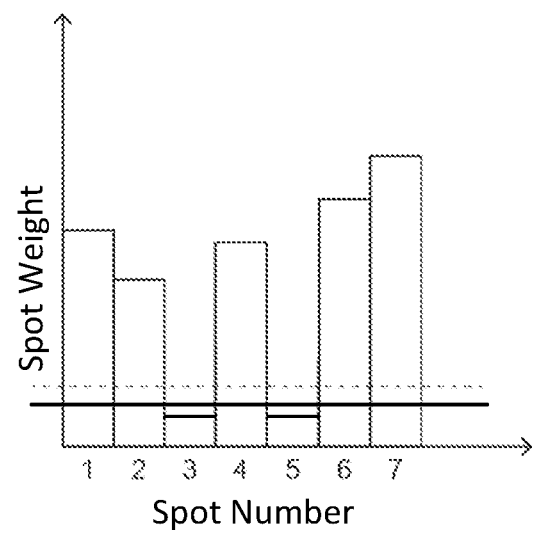
FIGURE 2b

SYSTEM AND METHOD FOR RADIOTHERAPY TREATMENT PLANNING

This application claims the benefit of European Patent Application No. 18203596.4, filed Oct. 31, 2018, the entire contents of which is incorporated by reference herein.

TECHNICAL FIELD

The present invention relates to a system and a method for planning of ion radiotherapy treatment plans, such as proton radiotherapy treatment plans, in particular plans involving pencil beam scanning (PBS).

BACKGROUND

In PBS an ion dose is delivered to a patient using a discrete set of spots, which are organized in energy layers. Each spot in an energy layer corresponds to a lateral position defined in the beam delivery system, and has an assigned weight that specifies the number of particles to be delivered to that position. The ion beam can either be continuously on (quasi-discrete PBS or raster scanning) or turned off when moving between the spot positions (step-and-shoot PBS). The energy layers, spot positions and weights together constitute a PBS treatment plan. In inverse planning, the weights are used as optimization variables in an iterative optimization process to fulfil the planning objectives, which are commonly based on desired plan or beam doses in different regions within the patient When treating a patient, a delivery system is used to deliver the right number of particles from each spot, according to the treatment plan. Delivery systems typically have constraints in that they can only deliver spots with weights between a minimum and a maximum spot weight. This limitation can be in conflict with the preferred solution for a mathematically optimal plan that best fulfils the planning objectives. In particular, an optimized plan will often contain a number of spots with weights above zero but below the minimum value. In some cases, there may be a high number of such low-weight spots which the delivery system would not be able to deliver. The resulting dose could then deviate from the desired goal of the optimization. In cases where a particular region has a cluster of only low-weight spots, there is a risk that all spots in that area are undeliverable, and that the whole region would receive a too low dose.

Theoretically, this could be addressed by an optimal positioning of spots before the optimization starts. In practice, this is an almost impossible task. In reality spot positioning, and in particular the spacing, involves a trade-off. Spots positioned closely together ensures a high dose homogeneity, but also results in many low-weight spots, which the delivery system may not be able to handle.

One approach to solving the problem of a treatment plan containing undeliverable spots is by removing all spots that have weights below the minimum spot weight, after the optimization of the plan. Such solutions are described, for example, in Howard et al.: *Effects of minimum monitor unit threshold on spot scanning proton plan quality*, Med. Phys. 41 (9), September 2014. As explained above, and as illustrated in this paper, removing spots is not always unproblematic, especially if a number of low-weight spots are located close together, which is often the case.

A slightly different approach is to perform a filtering, that is, removal of spots after a certain number of iterations in the optimization. In this case a minimum value may be set, which can be equal to or lower than the minimum spot weight allowed by the delivery system, and only spots having a spot weight lower than this minimum value will be discarded. The optimization is then resumed and a number of iterations are performed now using only the spots that were kept in the filtering. This will normally lead to increased spot weights for remaining spots near the discarded spots. While this will often yield a better plan than simply removing all low-weight spots after optimization is finished, it is still a problem that too many spots may be removed in certain regions in the filtering step. In addition, there is no guarantee that the resulting spot weights from the resumed optimization will be above the minimum allowed spot weight.

An alternative solution, introduced in RayStation 4.5, involves applying, after the filtering step, a bound on the allowed spot weights in the optimization problem. This ensures that the plan will not comprise any spots having a lower weight than allowed. Cao et al., *Incorporating deliverable monitor unit constrains into spot intensity optimization in intensity modulated proton therapy treatment planning*, Phys Med Biol. PMC 2014, Aug. 7, describes a similar solution, in which spot intensities are optimized and all spots having a weight of zero after this first optimization are discarded. In a subsequent optimization, a constraint is placed on all spot weights, so that each spot weight must be higher than B, B being a fraction of the real minimum value. The results from these two solutions are comparable to the methods outlined above, and the same problem with too many spots being filtered out remains.

SUMMARY

It is an object of the present invention to minimize the influence of the constraints of the delivery system on the quality of a radiation therapy treatment plan. In particular the invention seeks to minimize the negative effects of constraints regarding spot weights.

The invention relates to a method of optimizing a radiation treatment plan, comprising the following steps, performed in a computer:
a) Running an optimization in order to distribute a desired dose over a predefined set of spots, wherein said optimization involves assigning a spot weight to each of the predefined spots, depending on the desired dose to that spot,
b) Interrupting the optimization,
c) Identifying at least a first and a second low-weight spot, said low-weight spots having spot weights below a first threshold,
d) Discarding the second identified low-weight spot from the set of spots while keeping the first identified low-weight spot in the set of spots, to obtain a reduced set of spots,
e) Resuming the optimization to obtain a radiation treatment plan in which the desired dose is delivered by the reduced set of spots.

The steps b) to e) may be repeated a suitable number of times.

In a preferred embodiment, the first threshold is selected as the minimum spot weight of the delivery system. In other embodiments it may be selected as a value below the minimum spot weight but higher than zero. It may also be selected as a value higher than the minimum spot weight of the delivery system, for example, to account for uncertainties in the delivery system.

According to the invention, therefore, some, but not all, low-weight spots are removed from the plan during optimization. This can be implemented in different ways, which all have in common the removal of some low-weight spots and a redistribution of spot weights to one or more other spots during the following optimization iterations. Test results have shown that such methods yield better plans than prior art solutions such as the ones discussed above. A certain fraction of all low-weight spots may be discarded, for example, the ones having the lowest weights. Alternatively, all low-weight spots having a weight below a threshold value lower than the minimum weight may be discarded. The removal of some low-weight spots in itself causes an increase in the spot weights of remaining spots in the plan during the subsequent optimization in step e), to maintain the desired dose level.

The method preferably further comprises the step of increasing the weight of at least one remaining spot to compensate for the weight of the discarded second low-weight spot, before resuming the optimization function. It is feasible, but not necessary, to increase the spot weights of one or more remaining spots before continuing the optimization, to facilitate the redistribution of spot weights. This may be done based on the spot weights of the discarded spots, or according to some other suitable rule. In a simple embodiment, the weights of all remaining low-weight spots in the reduced set of spots may be increased up to a certain weight, such as the minimum spot weight or a certain fraction of the minimum spot weight, for example, 80% or 90% of the minimum spot weight. The weights of one or more removed spots may be redistributed to one or more remaining spots, or to one or more new spots added to the set of existing spots.

In a preferred embodiment, the spot weight assigned to a spot that is discarded is reassigned to another, second, spot before the optimization continues. The second spot may be chosen randomly, or it may be selected based on proximity to the discarded spot in some measure constructed from the spot positions in either geometric or radiologic distance, spot energy, spot weights, or the spot dose distributions. In a preferred embodiment, the spots are ordered in a set of spots and the spot weights from discarded spots are added to the next spot in the set. It is also possible to identify the next low-weight spot in the set and add the spot weight of the discarded spot to the next low-weight spot in the set. This may be repeated until the sum of the spot weights assigned to a low-weight spot exceeds a second threshold value and this low-weight spot will be kept in the set. Alternatively, the second spot may be selected based on proximity to a geometric or a radiological center of gravity between a number of discarded spots, weighted by the weights of the discarded spots.

A preferred embodiment comprises the steps of identifying and discarding the lowest weighted spot in the predefined set of spots and redistributing its weight to another spot and repeating this step for a new lowest weighted spot, that is, identifying and discarding the new lowest weighted spot and redistributing its weight to another spot. This may be repeated a suitable number of times. In this way, the lowest-weighted spots will be discarded, and their weights will be redistributed.

The position of the second spot may be selected within the energy layer of the discarded spot or in another existing energy layer. The weight of the second spot is recalculated as a function, most simply the sum, of its original weight and the weight of the spot that has been removed. The second spot may be kept in the reduced set of spots, or it may be discarded in a subsequent step and its weight reassigned to a third spot. The method is chosen to facilitate the redistribution of spot weights during the continued optimization. It is of course possible that the second spot weight is recalculated to include the weight of more than one discarded spot. It would also be possible to distribute the spot weight of the discarded spot over several other spots. It would also be possible, if more than one low-weight spot is discarded, to accumulate the spot weights and reassign them in such a way as to conserve the total sum of the spot weights, while distributing it more favorably over the remaining spots.

In some embodiments, one or more new spots not in the predefined set of spots may be defined and spot weights of discarded spots may be reassigned to these new spots. In such embodiments, the method includes the step of determining a longitudinal position in a new or existing energy layer and lateral position within the selected energy layer for a new spot and assigning a spot weight to the new spot to compensate for one or more discarded spots. This enables the selection of an optimal position for a new spot, which may be selected, for example, based on a geometric or radiological center of gravity between a number of discarded spots, preferably weighted by the weights of the discarded spots.

The end result of the proposed solutions is plans of higher quality, with dose distributions that are closer to the desired optimization result also in the presence of minimum spot weight limitations. This is true in particular for areas of the target volume where the presence of spots of low weight are necessary to obtain the desired dose distribution. The resulting plans are less sensitive to a final removal of low-weighted (undeliverable) spots. The resulting plans are also more robust against the choice of initial spot distribution parameters, such as energy layer spacing and lateral spot spacing. For example, the result is stable even when too many spots are placed in the target initially, which makes it possible to explore an optimal spot distribution with smaller spacing, leading to possible improvements in plan quality. Similarly, the resulting plans are less sensitive to the precise machine limit on minimum spot weight. The deviation from a mathematically optimal plan is a smoother function of the minimum spot weight, making the behavior more predictable.

The invention also relates to a computer program product comprising computer readable code means, preferably stored on a non-transitory storage medium, which, when run in a processor will cause the processor to perform the inventive method. The invention also relates to a computer system comprising a processor, a data memory and a program memory, wherein the program memory comprises a computer program product according to the above, arranged to be run in the processor to control radiotherapy treatment planning.

BRIEF DESCRIPTION OF THE DRAWINGS

The invention will be described in more detail in the following, by way of example and with reference to the appended drawings, in which FIGS. 1a, 1b and 1c are schematic representations of an energy layer in an ion PBS plan. FIG. 1a shows the initial distribution of spots, FIG. 1b shows a resulting distribution of spots according to a prior art method and FIG. 1c shows a resulting distribution of spots according to the invention.

FIGS. 2a and 2b are histograms schematically illustrating the spot weights of a number of spots.

DETAILED DESCRIPTION

Figure 3:
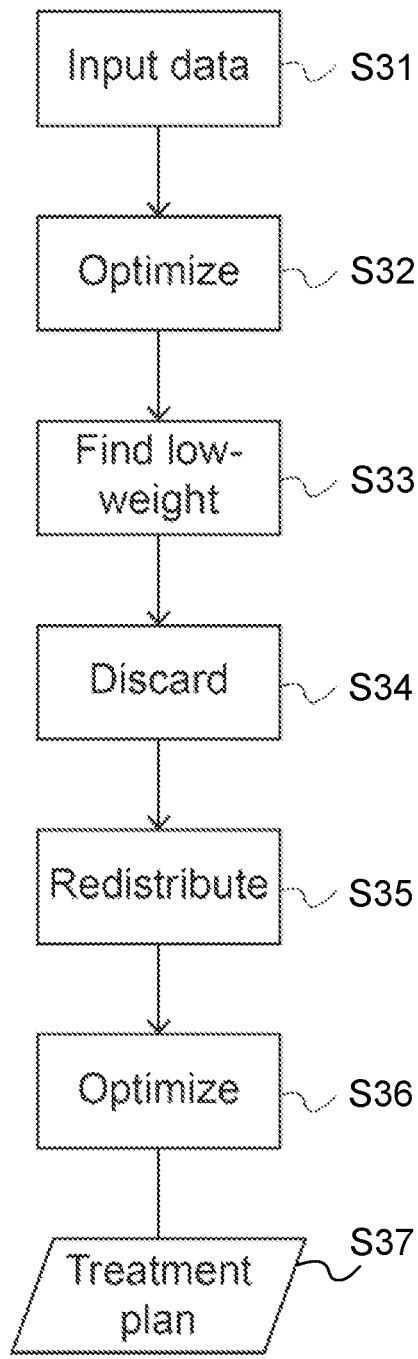
FIG. 3 is a flow chart of an overall embodiment of the method according to the invention.

FIG. 1a illustrates one energy layer of an ion PBS plan, with a set of initially defined spots, that is, the spots that are used from the beginning of the optimization procedure. The spots have defined lateral positions to which the ion pencil beams should be directed. Typically, in a complete plan, there are several such energy layers with different spot distributions, so that the dose delivered from the spots conform in three dimensions to the target shape. As can be seen, the spots in this example are distributed with uniform lateral spacing, which is typically the case. The positions and the spacing between the spots may be determined in any suitable way by default values, or by a consideration of parameters such as the characteristics of the delivery system.

FIG. 1b illustrates the spot distribution within the same energy layer after plan optimization and filtering according to the prior art. All spots having a spot weight below the minimum spot weight of the delivery system have been filtered out (removed). As can be seen, there is a significant central area where almost all spots had a spot weight below the minimum spot weight. This typically occurs when spots from more distal (higher energy) layers deposit dose in the same region. Since all spots have been discarded in this region, there is no possibility to adjust the dose using these spots to fulfill the optimization objectives. In some prior art systems, this would be the end result for the plan. In other prior art systems, this would be the starting point for further optimization. In the latter case, the further optimization would likely attempt to compensate for this by increasing the spot weights of the remaining spots in and immediately surrounding the central, empty area. However, in both cases, the discarded spots would be permanently gone, and the likely next step would be to go back to the beginning and restart spot placement.

FIG. 1c illustrates the spot distribution within the same energy layer after plan optimization according to an embodiment of the invention. As can be seen, only some of the low-weight spots in the central area have been discarded, while others have been retained. When the spot weights of the remaining spots in this central area are recalculated to compensate for the dose that is lost when some spots are discarded, there is a greater chance that each of the remaining spots in this area will have a weight above the minimum spot weight. The result is a more even dose distribution than according to the prior art, in particular in the central area which had a lot of low-weight spots after some iterations of the optimization algorithm.

FIG. 2a is a histogram showing the spot weights of seven spots numbered 1-7, to serve as a simplified example of how to select which spots to discard or keep, respectively. A horizontal dashed line marks the minimum spot weight handled by the delivery system to be used. As can be seen, in this example, spots 3 and 5 have spot weights below the minimum spot weight. Therefore, according to the present invention, one of them should be discarded and one should be kept. In a real situation, of course, there will be a higher number of spots, and a higher number of low-weight spots. Some of these low-weight spots should be discarded and some should be kept. The removal of a fraction of low-weight spots will in itself cause the spot weights of adjacent remaining spots to increase in subsequent optimization steps. As will be discussed below, within a group of low-weight spots having some proximity to each other, it is advantageous to add the spot weight of the discarded spot to the spot weight of the low-weight spot that is kept, to increase the chances that the spot weight of this latter spot will be above the minimum spot weight.

FIG. 2b is a histogram showing the same spot weights and the same minimum spot weight as FIG. 2a, again to serve as a simplified example. In FIG. 2b there is also a minimum threshold, indicated by a solid line, which is higher than zero and lower than the minimum spot weight. This will enable further adapted processing of spots. For example, it may be decided to discard completely all spots having weights below the minimum threshold and keep the spots that have weights above the minimum threshold. Again, the weights of the low-weight spots that are kept are preferably, but not necessarily, increased. If the low-weight spots have some proximity to each other, a suitable way of achieving this will be by addition of the spot weights of discarded low-weight spots.

FIG. 3 is an overall flow chart of one method of the invention. As is common in dose planning, one or more images of a patient are used as input data. In a first step S31, input data are provided, including a set of spots and their initial spot weights, an optimization function and a minimum threshold for the spot weights. The optimization function uses spot weights as variables. The person skilled in the art is familiar with how to define optimization functions. The minimum threshold may be equal to the minimum spot weight of the delivery system, or may be set to a suitable value. The value may be a value between zero and the minimum spot weight. If the minimum threshold is lower than the minimum spot weight, fewer spots will be marked as low-weight spots during the process. The value may also be a value above the minimum spot weight of the delivery system, for example to account for uncertainty in the delivery system by avoiding spots having weights close to the minimum value. In a second step S32, the optimization is run a number of iterations in a conventional manner. In a third step S33 any low-weight spots, that is, spots having a spot weight lower than the minimum threshold, are identified. It may facilitate the further processing if any area having a high fraction of low-weight spots is also identified. In the situation shown in FIGS. 1a, 1b and 1c, this would be the central area, which consists predominantly of low-weight spots. In the next step S34 some of the low-weight spots are discarded. How many, and which spots to discard may be determined in different ways, as will be discussed below.

Step S35 is an optional step, in which the spot weights of the remaining low-weight spots are increased. This may be done by redistributing the spot weights of the discarded spots to one or more of the remaining spots, preferably to remaining low-weight spots. How to redistribute the spot weights may be determined in a number of different ways, as will be discussed below. In step S36, the optimization continues with at least one subsequent iteration, until the final treatment plan has been optimized and is output as S37. During this continued iteration of the optimization, the spot weights will be redistributed between the remaining spots as the optimization will compensate for the dose that is lost because of discarded spots. Step S35, if performed, will facilitate the redistribution in step S36.

In step S33, the method may be set to identify all spots having a spot weight below a minimum threshold value, which may be the minimum spot weight or a value between zero and the minimum spot weight. It may also be a value above the minimum spot weight. Alternatively, the method may be set to identify the N spots having the lowest spot weight, N being a specified number of spots, or a fraction of the total number of spots. If the minimum threshold value is set to a value between zero and the minimum spot weight, it may be possible to discard all spots having weights below the minimum threshold, since the low-weight spots having a weight between the minimum threshold and the minimum spot weight will remain.

In step S34 some of the low weight spots are discarded. In the general case, some of the low-weight spots are also kept. How many spots to discard and how many to keep may be determined in a number of different ways. In one preferred embodiment, a specific fraction, for example, 20, 30, 40 or 50% of the low-weight spots may be discarded. Which individual spots to discard may be determined in different ways, for example, randomly, or every second, third or fourth low-weight spot may be discarded. Alternatively, the decision on which spots to discard may be based on spot positions, either within an energy layer or globally, spot dose information, target or risk organ geometry, or any other plan parameter. Alternatively, among the low-weight spots, the spots may be ordered by their weights and the spots having the lowest weights may be discarded.

According to one embodiment the lowest weighted spot is discarded and its weight redistributed to another spot. Then, the new lowest weighted spot is discarded and its weight is redistributed to another spot. This procedure is repeated until there are no remaining spots having a weight lower than the minimum threshold. The spots to which to redistribute the weights of the discarded spots may be selected in any suitable way.

The redistribution of weights in optional step S35 may be achieved in different ways. The low-weight spots considered together for redistribution should be located near, and preferably adjacent, to each other in some measure that takes into account the geometrical distribution of spots, in 2D or 3D. This measure may be related to geometrical or radiological distance, possibly weighted by a function of the spot weights of the spots concerned. In the simplest case, the spot weights of all remaining spots are increased for example by a certain value, a certain fraction, or up to a certain value, which may be determined in any suitable way, for example, related to the minimum spot weight. This increase could also be determined with consideration of the ratio between discarded spots and low-weight spots that are kept.

The redistribution of spot weights may also take into account information on the patient geometry, typically from the CT images and delineated regions of interest. For example, this information may be used to handle spots inside the target in a different way from spots outside of the target. One possible rule could be that spots outside of the target may be removed without any redistribution of their spot weights while spots within the target may not be removed without redistribution of their spot weighs to one or more other spots within the target.

Preferably, the spot weights of remaining spots are increased with consideration of the spot weights of one or more discarded spots. One simple way to achieve this is to number all spots, or all spots identified in step S33 as low-weight spots. When a first low-weight spot is encountered, the process proceeds to identify the next spot according to the numbered order. Alternatively, the next spot could be identified by examining all spots adjacent to the first low-weight spot to select an adjacent spot. In both cases, the first low-weight spot is then discarded, and its weight is added to the weight of the next spot. It will also be possible to discard more than one spot in a sequence of low-weight spots and add all the weights of the discarded spots to one low-weight spot in the sequence. This one low-weight spot may be selected in any suitable way, including as the first or the last one spot in the sequence, a spot near the middle of the sequence or a random spot within the sequence. It may also be selected as the spot in the sequence of spots having the highest, or the lowest spot weight before the addition, or the spot weight nearest to an average of the low-weight spots. The method may be arranged to add the weights of a predetermined number of spots, for example three, four or five, or may be arranged to continue discarding more spots and adding their spot weights, until the total spot weight of the spot that is kept is above a threshold, which is typically but not necessarily the minimum spot weight.

It would also be possible in step S35 to redistribute spot weights of one or more discarded spots over more than one spot. The spot weights of one or more discarded spots may also be distributed over a number of spots that are initially above the minimum threshold. This may be useful, for example, in an embodiment where spot weights from a group of discarded spots are accumulated but do not reach the minimum spot weight. In this case, all spots in that group might be discarded and their accumulated spot weight may be assigned to one nearby spot that already has a spot weight above the minimum threshold, or may be distributed over a number of such spots. For example, the redistribution may be made to make the spot weights of all remaining spots more equal. Alternatively, the redistribution may be made so that a higher fraction of the redistributed spot weight is added to spots having a lower or higher spot weight to begin with. The redistribution of spot weights may be made with consideration of the dose distributions of the remaining spots over which the spot weights are redistributed.

It should be noted that a group of discarded spots considered together may comprise spots from only one energy layer, or from different energy layers, if the discarded spots from the different energy layers have some kind of proximity to each other. As mentioned above, the proximity may be based on geometric distance or radiological distance, possibly weighted according to the spot weights of the spots concerned. Proximity may also be generalized to take into account e g similarity measures on the dose distributions of the spots concerned.

Figure 4:
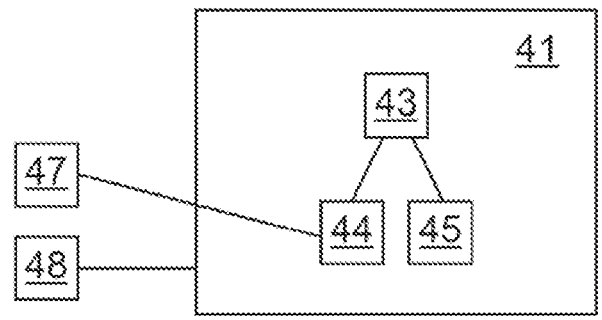
FIG. 4 shows schematically a computer system which may be used to perform the method.

FIG. 4 is a schematic drawing of a computer system in which the method according to the invention may be performed. A computer 41 comprises a processor 43, a data memory 44 and a program memory 45. Preferably, one or more user input means 47, 48 are also present, in the form of a keyboard, a mouse, a joystick, voice recognition means or any other available user input means. The user input means may also be arranged to receive data from an external memory unit.

The data memory 44 comprises data to be used in the procedure, such as the precalculated plans and clinical goals. The program memory 45 holds a computer program arranged to make the computer perform the method steps discussed in connection with FIG. 3.

As will be understood, the data memory 44 and the program memory 45 are shown and discussed schematically. There may be several data memory units, each holding one or more different types of data, or one data memory holding all data in a suitably structured way, and the same holds for the program memories. For example, there may be separate memories or memory segments for precalculated plans, clinical goals and combined plans, respectively. One or more memories may also be stored on other computers.

In the previous discussions, it has been assumed that spots can be discarded, because of low spot weights but that no spots can be added to the set of spots initially defined. It will, however, also be possible to define one or more new spots and to redistribute spot weights from one or more discarded spots to such new spots. A new spot is preferably selected to replace a number of discarded spots, in dependence of the locations and weights of the discarded spots. For example, a geometric center of gravity between the positions of the discarded spots, preferably weighted according to their respective spot weights, may be used as the new spot position. The new spot position may also be determined with consideration of radiological depth, CT geometry, spot- and total dose distributions, spot characteristics or any plan parameter such as spot spacing. A new spot position may also take into account the positions of one or more spots that are not discarded, for example, by increasing the distance to a spot having a high weight. Even in a case where all discarded spots are located in the same energy layer, a new spot position is not necessarily defined in that energy layer; it may be more feasible to place it in a different energy layer. Hence, the new spot may be placed in the nearest existing energy layer, or in a new energy layer.

The invention claimed is:

1. A method of optimizing a radiation treatment plan of ion treatment by a computer, comprising:
   a) running an optimization in order to distribute a desired dose over a predefined set of spots, wherein said optimization involves assigning a spot weight to each of the predefined spots, depending on the desired dose delivered from the respective spot;
   b) interrupting the optimization;
   c) identifying at least a first low-weight spot and a second low-weight spot, said low-weight spots having spot weights below a first threshold;
   d) discarding the second low-weight spot from the set of spots while keeping the first low-weight spot in the set of spots, to obtain a reduced set of spots;
   e) adding the spot weight of the second low-weight spot to the spot weight of the first low-weight spot to compensate for the spot weight of the second low-weight spot;
   f) resuming the optimization to obtain a radiation treatment plan with the reduced set of spots;
   g) repeating b) through f) at least once until a sum of spot weights assigned to any one of the low-weight spots exceeds a second threshold; and
   h) communicating the radiation treatment plan to a beam delivery system and configuring the beam delivery system to deliver the desired dose using the reduced set of spots based on the radiation treatment plan.

2. The method according to claim 1, further comprising:
   identifying a number of low-weight spots including the first and second low-weight spots; and
   discarding a certain fraction of the number of low-weight spots, wherein the certain fraction includes the second low-weight spot.

3. The method according to claim 2, further comprising:
   discarding more than one of the low-weight spots that are identified, and
   adding spot weights of the more than one of the low-weight spots to at least one remaining spot of the low-weight spots.

4. The method according to claim 3, wherein spot weights below the second threshold are added to the at least one remaining spot until the sum of the spot weights exceeds the second threshold.

5. The method according to claim 3, wherein the predefined set of spots are in a numbered order, and the at least one remaining spot is selected as a next low-weight spot in the numbered order such that the spot weight of the second identified low-weight spot is added to a spot weight of the next low-weight spot as selected.

6. The method according to claim 3, wherein the at least one remaining spot is selected based on proximity to a geometric center of gravity between a number of discarded spots, weighted by the weights of the discarded spots.

7. The method according to claim 2, wherein the second low-weight spot is a lowest weighted spot in the predefined set of spots, and the method further comprising:
   redistributing a weight of the lowest weighted spot to another spot in the predefined set of spots.

8. The method according to claim 1, further comprising determining a position for a new spot and assigning a spot weight to the new spot to compensate for one or more discarded spots.

9. The method according to claim 8, wherein the position for the new spot is determined based on a geometric center of gravity between a number of discarded spots, weighted by the weights of the discarded spots.

10. The method according to claim 8, wherein the position for the new spot is determined based on a radiological depth of a number of discarded spots.

11. The method according to claim 8, wherein the position for the new spot is in a second energy layer different from a first energy layer in which the one or more discarded spots is located.

12. A non-transitory storage medium storing thereon a computer program with instructions, which, when run in a processor, causes the processor to perform the method according to claim 1.

13. A computer system comprising the processor, a data memory, and a program memory comprising the storage medium according to claim 12.

14. A method of optimizing a radiation treatment plan of ion treatment by a computer, comprising:
   a) running an optimization in order to distribute a desired dose over a predefined set of spots, wherein said optimization involves assigning a spot weight to each of the predefined spots, depending on the desired dose delivered from the respective spot;
   b) interrupting the optimization;
   c) identifying low-weight spots, said low-weight spots having spot weights below a threshold;
   d) discarding a fraction of the low-weight spots from the set of spots while keeping remaining spots of the low-weight spots in the set of spots, to obtain a reduced set of spots;
   e) adding spot weights of the discarded spots to at least one of the remaining spots, wherein the at least one of the remaining spots is selected based on proximity to a geometric center of gravity between the discarded spots, weighted by the spot weights of the discarded spots;
   f) resuming the optimization to obtain a radiation treatment plan with the reduced set of spots; and
   g) communicating the radiation treatment plan to a beam delivery system and configuring the beam delivery system to deliver the desired dose using the reduced set of spots based on the radiation treatment plan.

15. A method of optimizing a radiation treatment plan of ion treatment by a computer, comprising:
   a) running an optimization in order to distribute a desired dose over a predefined set of spots, wherein said optimization involves assigning a spot weight to each of the predefined spots, depending on the desired dose delivered from the respective spot;

b) interrupting the optimization;

c) identifying low-weight spots, said low-weight spots having spot weights below a threshold;

d) discarding a fraction of the low-weight spots from the set of spots while keeping remaining spots of the low-weight spots in the set of spots, to obtain a reduced set of spots;

e) determining a position for a new spot based on a geometric center of gravity between the discarded spots, weighted by the weights of the discarded spots, wherein a new spot weight is assigned to the new spot to compensate for one or more of the discarded spots;

f) resuming the optimization to obtain a radiation treatment plan with the reduced set of spots; and g) communicating the radiation treatment plan to a beam delivery system and configuring the beam delivery system to deliver the desired dose using the reduced set of spots based on the radiation treatment plan.

16. A method of optimizing a radiation treatment plan of ion treatment by a computer, comprising:

a) running an optimization in order to distribute a desired dose over a predefined set of spots, wherein said optimization involves assigning a spot weight to each of the predefined spots, depending on the desired dose delivered from the respective spot;

b) interrupting the optimization;

c) identifying a number of low-weight spots, said low-weight spots having spot weights below a first threshold;

d) discarding a certain fraction of the identified low-weight spots from the set of spots while keeping remaining low-weight spots of the identified low-weight spots in the set of spots, to obtain a reduced set of spots;

e) adding spot weights of the discarded low-weight spot that are below a second threshold to at least one spot weight of at least one of the remaining spots until a sum of the spot weights assigned to the at least one of the remaining spots exceeds the second threshold value;

f) resuming the optimization to obtain a radiation treatment plan with the reduced set of spots; and g) communicating the radiation treatment plan to a beam delivery system and configuring the beam delivery system to deliver the desired dose using the reduced set of spots based on the radiation treatment plan.

\* \* \* \* \*